United States Patent

Benziger et al.

[11] Patent Number: 5,728,360
[45] Date of Patent: Mar. 17, 1998

[54] VANADYL PYROPHOSPHATE PRECURSORS

[75] Inventors: Jay B. Benziger, Lawrenceville; V. Vance Guliants, Princeton; Sankaran Sundaresan, Mercerville, all of N.J.

[73] Assignee: The Trustees of Princeton University, Princeton, N.J.

[21] Appl. No.: 559,002

[22] Filed: Nov. 16, 1995

Related U.S. Application Data

[62] Division of Ser. No. 338,237, Nov. 14, 1994, Pat. No. 5,532,385.

[51] Int. Cl.$^6$ ................................ C01B 25/16
[52] U.S. Cl. ................................ 423/307
[58] Field of Search ................................ 423/307, 305

[56] References Cited

U.S. PATENT DOCUMENTS 4,518,534  5/1985  Johnson et al. ............... 260/429 R

OTHER PUBLICATIONS

Silha et al, "Herstellung Und Untersuchung Von Phosphiten XVII, Vanadylphosphite", Collection of Czechoslov. Chem. Comm., vol. 32, 1967 (no month).

Chemical Abstract: 67: 87296f "Preparation & Study of Phosphites", 1967 (no month).

Chemical Abstract: 122: 70674j "Synthesis & crystal structure of vanadyl phosphite [VO(HPO3) (H$_2$O)$_2$]$_n$·3n H$_2$O", Feb. 1995.

Chemical Abstract: 67: 111868s "Preparation & study of phosphites", 1967 (no month).

*Primary Examiner*—Ngoc-Yen Nguyen
*Attorney, Agent, or Firm*—Woodbridge & Associates

[57] ABSTRACT

The composition of matter, vanadyl phosphite, useful as a precursor to a vanadium/phosphorous oxide oxidation catalyst used in the selective oxidation of n-butane to produce maleic anhydride.

1 Claim, 1 Drawing Sheet

VANADYL PYROPHOSPHATE PRECURSORS

This is a divisional of application Ser. No. 08/338,237 filed on Nov. 14, 1994 now U.S. Pat. No. 5,532,385.

The present invention relates to new vanadium/phosphorus oxide oxidation catalyst precursors and their method of use.

BACKGROUND OF THE INVENTION

The production of maleic anhydride is an important process in the fields of petrochemicals and polymer feedstocks. Maleic anhydride is produced, inter alia, by the selective oxidation of n-butane, available for example from petroleum refinery streams. See e.g., U.S. Pat. No. 4,351,773. The Vanadium-phosphorus-oxide (VPO) system is a well known commercial catalyst for the partial oxidation of $C_4$ hydrocarbons, particularly n-butane, to maleic anhydride. The VPO system is important as a highly selective and active catalyst. The most effective catalyst, vanadyl pyrophosphate, is produced during the pyrolysis of vanadyl (IV) hydrogen phosphate hemihydrate (VHP). The catalyst precursor, VHP, is converted to the pyrophosphate catalyst by calcination in nitrogen, in the absence of oxygen, at ca. 823° K. The structural similarity between vanadyl pyrophosphate and its pyrolitic precursor is manifested in the presence of vanadyl dimers, $V_2O_8$, in both structures connected through corners by $P_2O_7$ or $HPO_4$ groups, respectively.

A variety of such catalysts and methods for their production have been described.

U.S. Pat. No. 3,864,280 describes a crystalline phosphorus-vanadium mixed oxide hydrocarbon oxidation catalyst in which the vanadium has an average valence of from +3.9 to +4.6, the P:V ratio is from 0.9:1 to 1.8:1, and the B-phase content is at least 25%.

U.S. Pat. No. 4,043,943 describes forming a phosphorus-vanadium-oxygen precursor by calcining an intermediate obtained by reacting a vanadium compound with phosphorus compound in an oxygen-containing solvent containing less than 20% water.

U.S. Pat. No. 4,100,106 describes a process in which a water precipitated salt complex formed from tetravalent vanadium salt and orthophosphoric acid is calcined at a temperature of at least 300° C.

U.S. Pat. No. 4,116,868 describes a catalyst prepared by calcining a phosphorus-vanadium-oxygen precursor formed in the presence of a small amount of surfactant.

U.S. Pat. No. 4,132,670 describes a crystalline phosphorus-vanadium mixed oxide hydrocarbon oxidation catalyst in which the vanadium has an average valence of from +4.0 to +4.5, the V:P ratio is about 1:1, and the intrinsic surface area is from 1 $m^2/g$ to 10 $m^2/g$.

U.S. Pat. No. 4,288,372 describes a catalyst similar to that set forth in U.S. Pat. No. 3,864,280 but having a surface area greater than 10 $m^2/g$ and containing lanthanum as a promoter.

U.S. Pat. No. 4,337,174 describes forming a phosphorus-vanadium-oxygen precursor which, prior to calcining, is heated at 130° to 170° C. and dried.

U.S. Pat. No. 4,418,003 describes the formation of a phosphorus-vanadium oxide catalyst by reacting a vanadium compound with phosphorus pentoxide in an acidic alcoholic medium.

U.S. Pat. No. 4,769,477 describes an attrition-resistant phosphorus-vanadium oxide catalyst incorporating silicon dioxide.

Various other catalysts are specified in, for example, U.S. Pat. Nos. 4,062,873, 4,333,853, and 4,562,268.

According to the present invention, vanadyl phosphonates, $(VO)C_nH_{2n-1}PO_3 \bullet 1.51H_2O$ represent a new class of precursors for the production of vanadyl pyrophosphate. Based upon the behavior of magnetic susceptibility at low temperatures. The vanadyl phosphonates fall into one of two structural categories: "type A" with vanadyl-phosphorus-oxygen connectivities displaying corner sharing vanadyl octahedra and "type B" where face sharing vanadyl dimers give rise to antiferromagnetic exchange interactions at low temperatures.

There is a close structural relationship between vanadyl (IV) hydrogen phosphate hemihydrate and "type B" phosphonates based upon the presence of the face sharing vanadyl dimers. The structure of the phosphonate is determined by packing constraints on the alkyl group, $C_nH_{2n+1}$. When the cross sectional area of the alkyl group exceeds 36 $Å^2$ the more open "type A" structure results. Of the "type B" phosphonates, three alkyl phosphonates, $VORPO_3 \bullet solvent$ where R is methyl, ethyl, and propyl, exhibit the same face sharing vanadyl dimer observed in layered vanadyl (IV) hydrogen phosphate hemihydrate. See e.g., J. W. Johnson et al. EP 134157 A2, 1985.

The present invention is a result of the discovery of (1) a new vanadyl phosphate with n=0, vanadyl phosphite and (2) the structural similarity of both the "type B" phosphonates and vanadyl phosphite and the conventional VHP catalyst precursor and the subsequent search for a method of converting these phosphonates to vanadyl pyrophosphate. The present invention relates to the synthesis of vanadyl phosphite and to the identification of new routes for converting the "type B" phosphonates to VPO catalysts that exhibit higher selectivity and conversion in the n-butane oxidation than found with catalysts prepared from the standard VHP precursor.

Thus, a catalyst precursor which can be directly added to the oxidation reaction and which has a low conversion temperature, high selectivity and high conversion for n-butane would be desirable. The compounds of the present invention exhibit higher selectivity and higher conversions than conventional organic catalysts, and their use results in a more efficient process for the production of maleic anhydride.

SUMMARY OF THE INVENTION

Vanadyl phosphonates having the formula $VOC_nH_{2n+1}PO_3 \bullet 1.5H_2O$ (n=0–4) represent a new family of precursors of the catalytic vanadyl pyrophosphate phase used in the selective oxidation of n-butane to maleic anhydride. These catalyst precursors are synthesized, e.g., by refluxing vanadium pentoxide, with anhydrous alcohol and the subsequent addition of $(C_nH_{2n+1})$-substituted phosphonic acid in the presence of a solvent and a small amount of mineral acid catalyst.

DETAILED DESCRIPTION OF THE INVENTION

Figure 1:
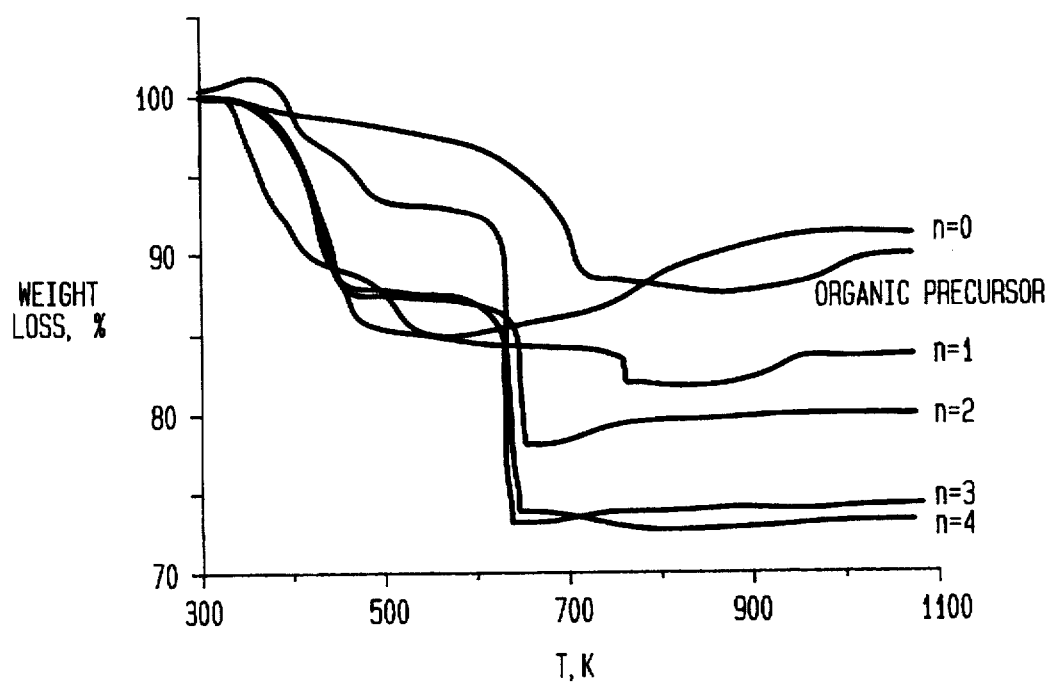
FIG. 1 is a graph representing the weight loss of catalyst precursors versus the temperature in degrees Kelvin.

The present invention pertains to a catalyst precursor which upon being calcined forms a low temperature vanadyl/phosphorus oxide oxidation catalyst of improved specificity. The precursor composition is represented by the general formula:

$$VOC_nH_{2n+1}PO_3 \cdot 1.5H_2O \qquad (I)$$

where n is equal to 0–4.

The invention also relates to the vanadium/phosphorus oxide oxidation catalyst formed by calcining the catalyst precursors of Formula I, and in the process of oxidation of lower hydrocarbons for the production of maleic anhydride using the catalyst so obtained.

The alkyl vanadyl phosphonate catalyst precursors of the present invention can be synthesized by processes generally known in the art. In one representative method, Vanadium pentoxide ($V_2O_5$) is refluxed with a reducing agent in a solvent for about 16 hours. During this period of time the color of the suspended solid changes from the orange of $V_2O_5$ to a light olive green. A solution of a ($C_nH_{2n+1}$)-substituted phosphonic acid, in an amount sufficient to yield a P/V molar ratio of about 0.8–1.3, in the same solvent is added along with a small amount of a mineral acid catalyst, e.g., HCl to facilitate the formation of vanadyl organophosphonates. The reaction mixture is refluxed for another 20 hours. The resulting light blue solids are separated by filtration, washed with acetone and dried in air.

The solvent used during synthesis is preferably a lower alcohol of $C_{1-4}$ and can also act as the reducing agent. If the solvent is not used as a reducing agent, an agent for the reduction of the vanadium (5+) cation is needed, for example, $SO_2$ or hydroquinone. When a large alcohol molecule, such as benzyl alcohol, is used as the solvent, the vanadyl phosphonates obtained exhibit the undesirable "type A" vanadyl octahedra structure. Alcohols with a cross-sectional area less than 36 Å$^2$ are necessary to obtain the desired "type B" vanadyl phosphonate.

Alternatively, vanadyl (IV) compounds, e.g., vanadyl sulfate and vanadyl acetylacetonate, can be used as a source of vanadium. In this method vanadyl sulfate trihydrate is added to an alcohol solution of phosphonic acid and refluxed for 48 hours to obtain a blue precipitate.

In contrast to the conventional catalyst precursor, the use of the vanadyl phosphonates of the present invention as catalyst precursors allows for the production of the catalyst in the same reaction vessel and at the same time as the partial oxidation of the hydrocarbon. The temperature at which the current VHP catalyst precursor is transformed into vanadyl (IV) pyrophosphate occurs at ca. 725° K. The new composition of the present invention, vanadyl phosphite (n=0), is transformed into the vanadyl pyrophosphate catalyst at a much lower temperature of ca. 523° K. In the case of vanadyl methylphosphonate the process of transformation to vanadyl (IV) pyrophosphate occurs at ca. 750° K., with the temperature progressively decreasing with the longer alkyl chain to ca. 600° K. for the butyl phosphonate. The crystallinity of the pyrophosphate phase decreases as the alkyl group becomes longer. This results in less ordered and even amorphous vanadyl pyrophosphate after the oxidation of the organic group as is the case with vanadyl propyl and butyl phosphonate.

The vanadyl phosphonates of the present invention are transformed to an active catalyst at much lower temperatures than the current VHP precursor. The conversion to the catalytically active vanadyl pyrophosphate at lower temperatures reduces the amount of undesired vanadium orthophosphate formed as a by-product. The presence of vanadium orthophosphate reduces the selectivity of the VPO catalyst for partial oxidation. The catalysts prepared from the vanadyl phosphite are the most selective catalysts. All of these catalysts possessed superior selectivity for partial oxidation of n-butane that catalysts derived from the standard VHP precursor.

These catalyst precursors are directly converted to the vanadyl pyrophosphate catalyst by the combined process of oxidation of the alkyl group and formation of the vanadyl pyrophosphate catalyst at temperatures ranging from about 500° K. to about 800° K. This thermal transformation can occur in air. In contrast, the common practice in the art requires the separate step of calcination of the VHP precursor in nitrogen, in the absence of oxygen. The attempt to convert the catalyst precursors of the present invention by the common practice of calcination in nitrogen would not yield the desired catalyst. The transformation of the catalyst precursors of the present invention is as follows:

$$2VOC_nH_{2n+1}PO_3 \cdot 1.5H_2O + (3n+1)O_2 \rightarrow (VO)_2P_2O_7 + 2nCO_2 + (2n+4)H_2O$$

Sample syntheses of the compounds of the present invention are presented in the following examples. These examples are presented to illustrate and are not intended to limit the scope of the present invention in any way.

EXAMPLE 1

Vanadyl phosphite

Vanadium pentoxide (5 g, Aldrich) was refluxed in anhydrous ethanol (100 ml, Aldrich) at 76° C. for sixteen (16) hours. During this period of time the color of The suspended solid changed from $V_2O_5$ orange to light olive green. A solution of phosphorous acid (5.27 grams, Aldrich) to yield a precursor with a phosphorus/vanadyl ratio of 0.93, in anhydrous ethanol (40 ml) was added along with a small amount (0.2 mL) of concentrated hydrochloric acid to act as a mineral acid catalyst to facilitate the formation of vanadyl organophosphates. The reaction mixture was refluxed at 76° C. for twenty (20) hours. The light blue solid was separated by filtration, washed with ethanol and dried in air. Elemental analysis confirmed the formula $VOHPO_3 \cdot 1.5H_2O$.

EXAMPLE 2

The synthetic method of Example 1 was followed, where, 4.5 grams of phosphorous acid was used to yield a precursor with a phosphorus/vanadyl ratio of 0.85.

EXAMPLE 3

The synthetic method of Example 1 was followed, where, 5.88 grams of phosphorous acid was used to yield a precursor with a phosphorus/vanadyl ratio of 1.15.

EXAMPLE 4

Vanadyl methylphosphonate

Following the synthetic process of Example 1, methylphosphonate with a bulk phosphorus/vanadyl ratio of 1.02 was made where in place of the phosphorous acid, 5.8 grams of methylphosphonic acid was used. Elemental analysis confirmed the formula $VOCH_3PO_3 \cdot 1.5H_2O$.

EXAMPLE 5

Vanadyl butylphosphonate

Following the synthetic process of Example 1 butyl phosphonate with a bulk phosphorus/vanadyl ratio of 0.96 was made where in place of the phosphorous acid, 7.58 grams of butyl phosphonic acid was used. Elemental analysis confirmed the formula $VOC_4H_9PO_3 \cdot 1.5H_2O$.

The phosphonates were characterized by X-ray diffraction. The X-ray diffraction pattern for vanadyl phosphite (VOHPO$_3 \cdot$1.5H$_2$O) is represented in Table I below.

TABLE I

X-ray Diffraction pattern of VOHPO$_3 \cdot$1.5H$_2$O.

| d-spacing Å | Intensity |
|---|---|
| 7.28 | 100 |
| 4.36 | 11 |
| 3.33 | 12 |
| 2.89 | 72 |
| 2.69 | 12 |
| 2.29 | 8 |

TGA curves using the catalyst precursors of the present invention (VOC$_n$H$_{2n+1}$PO$_3 \cdot$1.5H$_2$O) and conventional organic precursor (VHP) were obtained and compared as illustrated in FIG. 1.

The first weight loss in the catalyst precursors of the present invention, beginning at ca. 330° K. corresponds to the two (2) step loss of the intercalated and structural water molecules. The second weight loss begins at higher temperatures and corresponds to a combined process of oxidation of the alkyl group and formation of vanadyl pyrophosphate. In the case of vanadyl phosphite, the loss of interlayer water molecules is followed by the oxidation of P(III)—H into P(V)—OH groups with their further condensation to yield vanadyl pyrophosphate.

Figure 2:
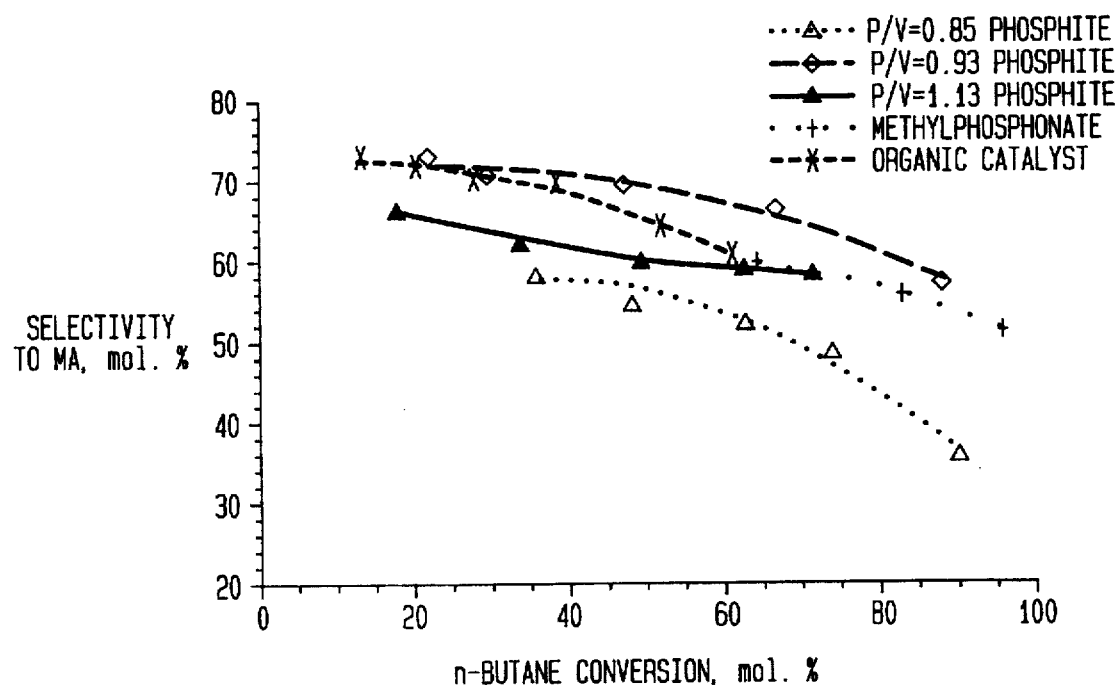
FIG. 2 is a graph representing the percent selectivity to maleic anhydride versus the percent n-butane conversion for various catalysts.

The catalytic performance of vanadyl phosphite and methylphosphonate in partial oxidation of n-butane to maleic anhydride in flow reactor studies was characterized. Three samples of vanadyl phosphite with different P/V ratios and vanadyl methylphosphonate with P/V equal to 1.02 were activated in the flow reactor and produced dependence of selectivity to maleic anhydride on n-butane conversion as shown in FIG. 2. For comparison, the selectivity-conversion relationship for a sample of the conventional organic catalyst prepared in accordance with U.S. Pat. No. 4,333,853 to Millberger et al., is also shown.

These results are summarized in Table II below.

TABLE II

Selectivity of VPO Catalysts at 381° C. in 1.2% butane in air at 62% conversion after 150 hours.

| Catalyst | Maleic Anhydride Selectivity (%) |
|---|---|
| Vanadyl Phosphite, P/V = 0.85 | 53 |
| Vanadyl Phosphite, P/V = 0.93 | 67 |
| Vanadyl Phosphite, P/V = 1.13 | 59 |
| Vanadyl Methylphosphonate | 60 |
| Standard Catalyst† | 61 |

†Prepared according to U.S. Pat. No. 4,351,773

Vanadyl methylphosphonate produced the VPO catalyst of similar performance to the conventional catalyst, while the P/V=0.93 vanadyl phosphite sample exhibited considerably higher selectivities than the organic catalyst at n-butane conversions above 40%. Under reaction conditions, the BET surface area of the methylphosphonate sample increased from 19 to 23.3 m$^2$/g, the surface area of P/V equals 0.85 and 1.13 vanadyl phosphite samples increased two-fold to high values of 40.9 and 43.4 m$^2$/g, while the most selective P/V=0.93 sample exhibited a three-fold increase of surface area to 37.7 m$^2$/g. The surface areas for conventional VPO systems generally do not exceed 20 m$^2$/g. The BET surface areas of the organic catalyst employed was 11.3 m$^2$/g.

It has successfully been shown that the compositions of formula 1 can successfully be used as precursors to vanadyl pyrophosphate catalyst. This new use for these compositions yield superior and more desirable C$_4$ oxidation to maleic anhydride than conventional catalyst precursors. Additionally, the new composition, vanadyl phosphite, is superior even to the n=1 to 4 organophosphonate samples.

What is claimed is:

1. The composition of matter having the chemical formula VOHPO$_3 \cdot$1.5H$_2$O.

* * * * *